United States Patent
DeMarsh et al.

(10) Patent No.: US 6,413,510 B1
(45) Date of Patent: Jul. 2, 2002

(54) DIMERIC MODIFIED GROβ PROTEIN

(75) Inventors: Peter Lawrence DeMarsh, West Chester; Kyung Oh Johanson, Bryn Mawr, both of PA (US)

(73) Assignee: SmithKline Beecham Corporation, Philadelphia, PA (US)

( * ) Notice: Subject to any disclaimer, the term of this patent is extended or adjusted under 35 U.S.C. 154(b) by 0 days.

(21) Appl. No.: 09/513,153

(22) Filed: Feb. 25, 2000

Related U.S. Application Data

(60) Division of application No. 08/846,966, filed on Apr. 29, 1997, now Pat. No. 6,042,821, which is a continuation-in-part of application No. PCT/US96/18616, filed on Nov. 20, 1996.
(60) Provisional application No. 60/007,425, filed on Nov. 21, 1995.

(51) Int. Cl.$^7$ .................... A61K 38/19; C07K 14/52; C12N 5/10; C12N 15/12; C12N 15/63
(52) U.S. Cl. .............. 424/85.1; 514/2; 514/8; 514/12; 530/324; 530/351; 435/69.5; 435/71.2; 435/252.3; 435/325; 435/320.1; 435/471
(58) Field of Search ................ 530/324, 351; 514/2, 8, 12; 424/85.1; 435/69.5, 71.1, 71.2, 471, 252.3, 254.11, 325, 320.1

(56) References Cited

PUBLICATIONS

G. Arturson, "Neutrophil granulocyte functions in severely burned patients", (1985) Burns, vol. 11, pp. 309–314.

Jansen et al., "Monocyte Chemotactic Protein 1 is Released during Lethal and Sublethal Bacteremia in Baboons", (1995), The Journal of Infections Disease, vol. 171, pp. 1640–1642.

Bossink, et al., "Plasma Levels of the Chemokines Monocyte Proteins–1 and –2 Are Elevated in Human Sepsis", (1995), Chemotactic vol. 86, No. 10, pp. 3841–3847.

K.E. Driscoll, "Macrophage Inflammatory Proteins: Biology and Role in Pulmonary Inflammation", (1994), Experimental Lung Research, vol. 20, pp. 473–490.

Burgmann, et al., "Serum Concentrations of MIP–1 α and Interleukin–8 in Patients Suffering from Acute *Plasmodium falciparum* Malaria", (1995), Clinical Immunology and Immunopathology, vol. 76, No. 1, pp. 32–36.

*Primary Examiner*—Prema Mertz
(74) *Attorney, Agent, or Firm*—Linda E. Hall; William T. King; Charles M. Kinzig

(57) ABSTRACT

The invention relates to the method of preventing and treating sepsis using chemokines selected from mature or modified KC [SEQ ID NO: 1], groα[SEQ ID NO:2], groβ [SEQ ID NO: 3] or groγ[SEQ ID NO: 4] or multimers thereof, alone or in conjunction with an anti-infective agent. This invention also relates to a new groβ dimer chemokine.

2 Claims, No Drawings

DIMERIC MODIFIED GROβ PROTEIN

RELATED APPLICATIONS

This is a divisional of application Ser. No. 08/846,966, filed Apr. 29, 1997, now U.S. Pat. No. 6,042,821, which is a continuation-in-part of Application Serial No. PCT/US96/18616, filed on Nov. 20, 1996, which claims the benefit of priority of Provisional Application Serial No. 60/007,425, filed Nov. 21, 1995.

FIELD OF INVENTION

This invention relates to the method of preventing and treating sepsis using certain chemokines alone or in conjunction with an anti-infective agent. This invention also relates to a new groβ dimer chemokine.

BACKGROUND OF INVENTION

Sepsis, as used herein, is broadly defined to mean situation when the invasion of a host by a microbial agent is associated with the clinical manifestations of infection including but not limited to: (1) temperature >38° C. or <36° C.; (2) heart rate >90 beats per minute; (3) respiratory rate >20 beats per minute or $PaCO_2$<32 mm Hg; (4) white blood cell count >12,000/cu mm, <4,000/cu mm, or >10% immature (band) forms; (5) organ dysfunction, hypoperfusion, or hypotension. Hypoperfusion and perfusion abnormalities may include, but are not limited to lactic acidosis, oliguria, or an alteration in mental states. (Chest 1992; 101: 1644–1566)

Sepsis can occur in hospitalized patients having underlying diseases or conditions that render them susceptible to bloodstream invasion or in burn, trauma or surgical patents. In many cases of sepsis, the predominant pathogen is *Escherichia coli*, followed by other Gram-negative bacteria such as the Klebsiella-Enterobacter-Serratia group and then Pseudomonas. Although comprising a somewhat smaller percentage of infection, Gram-positive microbes such as Staphylococcus and systemic viral and fungal infections are included by the term sepsis as used herein. The genitourinary trait is the most common site of infection, the gastrointestinal tract and respiratory tract being the next most frequent sources of sepsis. Other common foci are wound, burn, and pelvic infections and infected intravenous catheters.

A serious consequence of bacterial sepsis often is septic sock. Septic shock is characterized by inadequate tissue perfusion, leading to insufficient oxygen supply to tissues, hypotension and oliguria.

Septic shock occurs because bacterial products react with cells and components of the coagulation, complement, fibrinolytic and bradykinin systems to release proteases which injure cells and alter blood flow, especially in the capillaries.

Microorganisms frequently activate the classical complement pathway, and endotoxin activates the alternative pathway. Complement activation, leukotriene generation and the direct effects of bacterial products on neutrophils lead to accumulation of these inflammatory cells in the lungs, release of their proteolytic enzyme and toxic oxygen radicals which damage the pulmonary endothelium and initiate the adult respiratory distress syndrome ("ARDS"). ARDS is a major cause of death in patients with septic shock and is characterized by pulmonary congestion, granulocyte aggregation, hemorrhage and capillary thrombi.

Septic shock is a major cause of death in intensive care units. There are an estimated 200,000 cases per year of septic shock in the United States, and despite advances in technology (i.e., respiratory support) and antibiotic therapy, the mortality rate for septic shock remains in excess of 40%. In fact, mortality for established septic shock has decreased very little since the comprehensive description by Waisbren (Arch. Intern. Med. 88:467–488 (1951)). Although effective antibiotics are available, and there is an increased awareness of the septic shock syndrome, the incidence of septic shock the last several decades has actually increased. With the appreciation that antimicrobial agents have failed to completely abrogate septic mortality, it is clear that other agents must be developed to be used alone or in conjunction with antimicrobials in order to rectify the deficiencies of current established therapy.

SUMMARY OF THE INVENTION

This invention relates to a method of preventing or treating sepsis comprising administering to a human or non-human animal in need thereof amount of a protein derived from a chemokine selected from KC, groα, groβ, and groγ. Most preferably, the chemokines used in the method of the invention include modified KC [amino acids 5–72 of the full length protein, SEQ ID NO: 1], an groβ [amino acids 5–73 of the full length protein, SEQ ID NO: 3] or modified human groγ [amino acids 5–73 of the full length protein, SEQ ID NO: 4] or multimers thereof. Most preferred is a covalently bonded dimer of two modified groβ chemokines [amino acids 5–73 of the full length protein SEQ ID NO: 3]. Alternatively, the mature chemokines may be utilized in the method of the invention.

The method of the invention may be performed alone, or in conjunction with administration of an anti-infective agent.

This invention also relates to a new covalently bonded groβ dimer consisting of two modified human groβ chemokines [amino acids 5–73 of the full length protein SEQ ID NO: 3].

Other aspects and advantages of the present invention are described further in the following detailed description of the preferred embodiments thereof.

DETAILED DESCRIPTION OF THE INVENTION

It is the object of this invention to provide a new method of treatment of sepsis comprising administering to an animal in need thereof, including humans, an effective amount of a chemokine. The chemokines useful in the method of the invention include mature KC [SEQ ID NO:1], groα [SEQ ID NO:2], groβ [SEQ ID NO:3], groγ [SEQ ID NO:4], or the modified and multimeric proteins derived therefrom, which are described in detail in International Patent Application, Publication No. WO94/29341, incorporated by reference herein. Particularly desirable are the modified KC [amino acids 5–72 of SEQ ID NO:2], modified groβ [amino acids 5–73 of SEQ ID NO:3], modified groγ [amino acids 5–73 of SEQ ID NO:4], and a novel covalently bonded dimer of two modified groβ chemokines [amino acids 5–73 of SEQ ID NO:3].

Although all but the dimeric modified groβ have been previously described. Their use in prevention and treatment of sepsis has not been reported. It has now been discovered that mature KC [SEQ ID NO: 1], human groα [SEQ ID NO:2], human groβ [SEQ ID NO: 3 or human groγ [SEQ ID NO: 4], and, particularly the modifies and multimeric chemokines derived therefrom significantly increase the survival of animals challenged with lethal sepsis causing organisms. Treatment with a medicament or the compound of this invention, alone or in combination with an anti-infective agent prior to contemplated thoracic or abdominal surgery would be useful in reducing the likelihood of post-operative sepsis. It may also be used post-operatively for the treatment of sepsis caused by a variety of reasons as outlined previously.

As stated above, the proteins useful in preparing medicaments and in the methods of the invention include the mature chemokines, modified chemokines, and multimers thereof.

The term "mature chemokines" also known as "intercrines" as used herein defines the proteins conventionally referred to in the art as KC, groα, groβ, groγ. For convenience, the amino acid sequences of the murine protein KC which contains 72 residues is provided in SEQ ID NO:1. These sequences are available from Genbank, accession number J04596. The sequences of the human protein groα (aa 1–73) are provided in SEQ ID) NO:2. The sequences of the human protein groβ (amino acids 1–73) are provided in SEQ ID NO: 3. The sequences of the human protein groγ are provided in SEQ ID NO:4. The cDNA and amino acid sequences of groγ are so provided in International Patent Application, Publication No. WO 92/00326 (Jan. 9, 1992). These groγ sequences have further been published in International Patent Application, Publication No. WO 94/29341 (Dec. 22, 1994), which is incorporated by reference herein.

The term "modified chemokines" is defined as in the above-referenced International Application. The modified chemokines are derived from KC, groβ, groα, and groγ, more preferably from groβ, groα, and groγ, and most preferably from groβ. The modified chemokines include desamino proteins characterized by the elimination of between about 2 to about 8 amino acids at the amino terminus of the mature protein. Most preferably, the modified chemokines are characterized by removal of the first 4 amino acids at the amino- (N-) terminus. Optionally, particularly when expressed recombinantly, the desamino chemokines useful in this invention may contain an inserted N-terminal Met. The N-terminal methionine which is inserted into the protein for expression purposes, may be cleaved, either during the processing of the protein by a host cell or synthetically, using known techniques. Alternatively, if so desired, this amino acid may be cleaved through enzyme digestion or other known means. Particularly desirable modified chemokines include modified KC [amino acids 5–72 of SEQ ID NO: 1], modified human groβ [amino acids 5–73 of SEQ ID NO: 3] and modified human groγ [amino acids 5–73 of SEQ ID NO: 4].

Also included by the term modified chemokine are other analogs or derivatives of KC, groα, groβ, or groγ which share the biological activity of the mature protein. As defined herein, such analogs and derivatives include modified proteins also characterized by alterations made in the known amino sequence of the proteins, e.g., the proteins provided in SEQ ID NOS: 1–4. Such analogs are characterized by having an amino acid sequence differing from that of the mature protein by 8 or fewer amino acid residues, and preferably by about 5 or fewer residues. It may be preferred that any differences in the amino acid sequences of the proteins involve only conservative amino acid substitutions. Conservative amino acid substitutions occur when an amino acid has substantially the same charge as the amino acid for which it is substituted and the substitution has no significant effect on the local conformation of the protein or its biological activity. Alternatively, changes such as the introduction of a certain amino acid in the sequence which may alter the stability of the protein, or permit it to be expressed in a desired host cell may be preferred. Another characteristic of these modified proteins may be enhanced biological activity in comparison to the mature protein.

By the term "multimeric protein" or "multimer" is meant herein multimeric forms of the mature and/or modified proteins useful in this invention, e.g, dimers, trimers, tetramers and other aggregated forms. Such multimeric forms can be prepared by synthesis or recombinant expression and can contain chemokines produced by a combination of synthetic and recombinant techniques as detailed below. Multimeric may form naturally upon expression or may be constructed into such multiple forms. Multimeric chemokines may include multimers of the same modified chemokine. Another multimer may be formed by the aggregation of different modified proteins. Still another multimer is formed by the aggregation of a modified chemokine of this invention and a known, mature chemokine. Preferably, a dimer or multimer useful in the invention would contain at least one desamino chemokine protein and at least one other chemokine or other protein characterized by having the same type of biological activity. This other protein may be an additional desamino chemokine, or another known protein.

Dimers may also be covalently linked, or concatenated. Concatenated dimers are intertwined dimers containing interlocked, but technically non-covalently linked monomers. Both covalently bonded and concatenated dimers are SDS (sodium dodecyl/lauryl sulfate) non-dissociable dimers. Covalently bonded dimers may be determined via mass spec analysis. In one particularly desirable embodiment, the method of the invention utilizes a novel dimeric truncated groβ protein [amino acids 5–73 of SEQ ID NO:3], which is covalently linked and which is described in more detail below in Example 1. This invention also includes this novel dimer consisting of two modified human groβ chemokines [amino acids 5–73 of the full length protein SEQ ID NO: 3].

Desirably, the chemokines useful in the method of the invention are used in the preparation of medicaments and/or are useful in the form of a pharmaceutical composition. Thus, the chemokines can be formulated into pharmaceutical compositions and administered in the same manner as described in, e.g., International Patent Applications, Publication No. WO 90/02762 (Mar. 22, 1990) and Publication No WO94/29341 (Dec. 22, 1994).

These medicaments or pharmaceutical compositions useful in the method of the invention for preventing or treating sepsis contain an effective amount of a mature, modified or multimeric chemokine protein derived from KC [SEQ ID NO: 1], human groα [SEQ ID NO: 2], human groβ [SEQ ID NO: 3], human groγ [SEQ ID NO: 4] or dimeric truncated human groβ which is administered to an animal in need thereof. Particularly desired embodiments utilize the modified chemokines, or multimers thereof. Most preferred is the novel covalently bonded dimer consisting of two modified human groβ chemokines [amino acids 5–73 of the full length protein SEQ ID NO: 3]. These chemokine compositions may be administered alone or in combination with administration of other anti-infective agents.

Thus, a pharmaceutical composition is prepared using one or more of proteins derived from the KC [SEQ ID NO:1], groα [SEQ ID NO:2], groβ SEQ ID NO:3] or groγ [SEQ ID NO:4] proteins. Suitable pharmaceutical carriers are well known to those of skill in the art and may be readily selected. Currently, the preferred carrier is saline. Optionally, the pharmaceutical compositions of the invention may contain other active ingredients or be administered in conjunction with other therapeutics. For example, the compositions of the invention are particularly well suited for administration in conjunction with anti-infective agents.

Suitable anti-infective agents include, without limitation anti-microbial agents routinely used for the treatment of sepsis such as amino-glycosides (such as amikacin, tobramycin, netilmicin, and gentamicin), cephalosporins such as ceftazidime, related betalactam agents such as maxalactam, carbopenems such as imipenem, monobactam agents such as aztreonam; ampicillin and broad-spectrum penicillins, (e.g., penicillinase-resistant penicillins, ureidopenicillins or antipseudomonal penicillin or Augmentin) that are active against P. aeruginosa, Enterobacter species, indole-positive Proteus species, and Serratia. Also included within the definition of anti-infective agents are antifungal agents, amphotericin and the like as well as anti-viral agents such as famvir and acyclovir.

The chemokines described herein are useful in the treatment and prevention of sepsis in humans and other animals such as dairy cattle, horses, calves or poultry. To effectively treat a human or other animal a mature, modified or multimeric KC [SEQ ID NO: 1], groα [SEQ ID NO: 2], groβ [SEQ ID NO:3] or human groγ [SEQ ID NO: 4] or their multimers including a covalently bonded dimeric, truncated groβ amino acids 5–73 of SEQ ID NO:3) may be administered by injection in the dose range of about 10 fg/kg/dose to about 1 mg/kg/dose, or orally in the dose range of about 10 fg/kg body weight per dose to about 10 mg/kg body weight per dose; if administered by infusion or similar techniques, the dose may be in the range of about 10 fg/kg/dose to about 1 mg/kg/dose; if administered subcutaneously the dose may be in the range of about 10 fg/kg/dose to about 1 mg/kg/dose.

Depending on the patient's condition, the compounds of this invention can be administered for prophylactic and/or therapeutic treatments. In therapeutic application, the compound is administered to a patient already suffering from a disease in an amount sufficient to cure or at least partially arrest the disease and its complications. It may be given at any time after surgery, preferably prior to 24 hours after surgery. In prophylactic applications, a composition containing mature, modified or multimeric KC [SEQ ID NO: 1], groβ [SEQ ID NO: 2], groβ [SEQ ID NO:3] or groγ [SEQ ID NO: 4] or a multimer or covalently bonded dimer thereof, is administered to a patient not already in a disease state to enhance the patient's resistance. It may be given one day or one week prior to surgery, preferably one to two days prior to surgery. It may be administered parenterally or orally.

Single or multiple administrations of the compounds can be carried out with dose levels and pattern being selected by the treating physician. In any event, a quantity of the compounds of the invention sufficient to effectively treat the patient should be administered.

The chemokines useful in the methods of this invention may also be administered in conjunction with a separately administered conventional anti-infective as disclosed herein above, such a gentamicin, augmentin or ceftazidime. The particular anti-infective chosen should be one to which the infective organism is susceptible and is selected or modified during therapy as the infecting microorganism is more particularly identified.

Additionally, various adjunctive agents in the treatment of septic shock also may be useful in combination with the components of this invention. They include sympathomimetic amines (vasopressors) such as norepinephrine, epinephrine, isoproterenol, dopamine, and dobutamine; anti-inflammatory agents such as methylprednisolone anti-inflammatory agents such as indomethacin and phenylbutazone; and corticosteroids such as betamethasone, hydrocortisone, methyiprednisolone, or dexamethasone; anti-coagulants such as heparin, anti-thrombin III or coumarin type drugs for certain conditions and schedules; diuretics such as furosemide or ethacrynic acid; and antagonist of opiates and beta-endorphins such as naloxone; an antagonist of tumor necrosis factor or of interleukin-1; phenothiazines; anti-histamines; glucagon; a-adrenergic blocking agents, vasodilators; plasma expanders; packed red blood cells; platelets; cryoprecipitates; fresh frozen plasma; bacterial permeability protein; clindamycin; and antibodies to (lipid A), the J5 mutant of E. coli or to endotoxin core glycolipids. Methods for preparing such antibodies are described widely in the literature.

One of the most important aspects in the treatment of the clinical septic shock syndrome is its apparently intractable resistance to the effects of a variety of highly potent anti-microbial agents. Despite the development of newer anti-microbial agents, the overall incidence of clinical sepsis has increased, and mortality remains unacceptably high, often approaching 60% of diagnosed patients. The discovery of the increased survival with the treatment of the full length, modified and multimeric KC [SEQ ID NO: 1], groα [SEQ ID NO: 2], groβ [SEQ ID NO:3], or groγ [SEQ ID NO: 4] and especially the covalently bonded modified groβ dimer [amino acids 5–73 of SEQ ID NO: 3] both prophylactically and after infection provides a new and useful therapy of sepsis.

The biological activity of modified KC [SEQ ID NO: 1] modified human groβ [SEQ ID NO: 3], modified human groγ [SEQ ID NO: 4], and a dimeric modified human groβ are demonstrated by the following assays. These examples illustrate the preferred methods of the invention. These examples do not limit the scope of the invention.

Rats. Male Fischer 344 rats obtained from Taconic farms weighing 200 to 250 g. were utilized. The rats were housed 2 per cage in standard plastic caging and fed lab chow and water ad libitum.

Modified KC [SEQ ID NO: 1], modified human groβ [SEQ ID NO: 2] or modified human groγ [SEQ ID NO: 3] or multimers thereof, was prepared in E. coli by the method given in Example 1. The compound was dissolved in DPBS containing 0.5% heat inactivated autologous normal rat serum. The animals were dosed intraperitoneally with KC 24 hours and 2 hours before infection. Control animals were dosed with dilution buffer on the same schedule. Starting two hours after infection the rats were treated twice daily with subcutaneous gentamicin.

E. coli. A clinical isolate of E. coli isolated from sputum was utilized. The organisms were tested for antibiotic sensitivity by the disc-agar diffusion technique and found to be sensitive to gentamicin, ampicillin, cephalothin, chloramphenicol, kanamycin, tetracycline, trimethoprin/sulfamethoxazole and resistant to penicillin G, erythromycin, and vancomycin. The organism was animal passed in mice and subsequently recovered and plated onto MacConkey's agar. The reisolated organisms were grown overnight in brain-heart infusion broth, and then stored frozen at −70° C. The inoculate the fibrin clot, organisms from thawed stocks were inoculated into brainheart infusion broth and incubated overnight on a rotary shaker (120 rpm) an 37° C. The E. coli was harvested by centrifugation, washed 3× and finally resuspended in normal saline. The number or organisms was quantified by turbidimentry, and the concentration adjusted with normal saline. All inoculum sizes were based on viable counts determined by scoring colony forming units on MacConkeys agar.

Fibrin Clot. The *E. coli* infected fibrin clots were made from a 1% solution of bovine fibrinogen (Type 1-S, Sigma) in sterile saline. The clot was formed by adding sequentially human thrombin (Hanna Pharma.) bacteria, and fibrinogen solution to 24 well plastic plates, Bacterial numbers of 2.0 to $3.0 \times 10^9$ were used in inoculate the fibrin clots. The resulting mixture was then incubated at room temperature for 30 minutes before implantation.

Animal Model. The rats were anesthetized with ketamine/xylazine (40 mg/kg/5 mg/kg) after which the abdominal surfaced were shaved and a midline laparotomy performed. Bacterial peritonitis was induced by implanting a fibrin-thrombin clot containing *E. coli* into the abdominal cavity. After implantation the muscle layers were closed with 4-0 silk suture, and the wounds closed with surgical staples. The animals were closely observed, any animals obviously moribund were euthanized.

Gentamicin. Rats were treated subcutaneously with gentamicin sulfate (Elkins-Sinn, NJ) 5 mg/kg twice a day for five days.

Statistics. All continuously variable data are expressed as the percent survival from several pooled studies. The Fisher's Exact test was used to determine the statistical significance of the differences between the survival rates at 14 days. The differences between the groups were considered statistically significant at $p<0.05$

EXAMPLE 1

Production of Truncated KC and GROβ

A. Expression of Recombinant Truncated KC and Truncated Groβ.

When truncated murine KC (amino acids 5–72 of SEQ ID NO:1) and human groβ (amino acids 5–73 of SEQ ID NO:3) were expressed intracellularly in *E. coli*, the KC (amino acids 5–72 of SEQ ID NO: 1) retained the initiator Met. In order to produce the authentic N-terminal recombinant proteins, a specific cleavable tag was engineered at the N-terminus of truncated KC (amino acids 5–72 of SEQ ID NO:1). The coding sequences of truncated murine KC (amino acids 5–72 of SFQ ID NO:1) and truncated human groβ (amino acids 5–73 of SEQ ID NO:3) were each amplified by polymerase chain reaction (PCR) from plasmids containing complimentary DNA sequences using both a forward primer encoding an NdeI site and a reverse primer containing n XbaI site. For truncated KC (amino acids 5–72 of SEQ ID NO:1), a defined epitope tag (DET) site and an enterokinase cleavage site were also used. These PCR fragments were subcloned into the *E. coli* LPlL-dependent expression vector pEAKn (pSKF301 derivative) between NdeI and XbaI sites. Each polypeptide was expressed by chemical induction of the LPL promoter in a lysogenic strain of *E. coli* containing the wild type (ind+) repressor gene (cI+) AR120.

B. Solubilization and Refolding of Truncated GROβ Monomer and Dimer

*E. coli* LW cells, 400 g, were lysed in 4 liters of lysis buffer containing 25 mM sodium citrate pH 6.0,40 mM NaCl, 2 mM EDTA by two passages through a Microfluidics (model M110Y) homogenizer at 11,000 psi. The cell lysate was centrifuged at 17,000 g (one hour at 4° C.) and the supernatant was discarded.The ii soluble truncated groβ [amino acids 5–73 of SEQ ID NO:3] in lysate pellet was solubilized in 1.3 liters of buffer containing 50 mm Tris HCl pH 8.0, 2 M guanidine HCl, 20 mM DTT by stirring 2 hours at room temperature. Soluble truncated reduced groβ [amino acids 5–73 of SEQ ID NO:3] was recovered by centrifugation at 25,000 g and pellet was discarded. Guanidine HCl and DTT were removed from protein solution by exhaustive dialysis against 50 mM sodium citrate pH 6.0 containing 2 mM EDTA. Majority of *E. coli* proteins were precipitated during dialysis, while truncated reduced groβ stayed in solution. Upon centrifugation, groβ was >90% pure. Truncated groβ solution was concentrated to 3 mg/ml (Amicon YM3 membrane) and raised to pH 8.5 with 0.5 M Trizma base. Air oxidation of truncated groβ [amino acids 5–73 of SEQ ID NO:3] was performed by stirring for 24 hours at 4° C. Formation of monomer and dimer was monitored by Vydac C18 (Nest) using 20–40% linear gradient of acetonitrile in 0.1% TFA for 30 min.

C. Purification

When monomer and dimer formation reached maximum and no reduced form left, the reoxidation solution was adjusted to pH 6.5 with 10% acetic acid. Groβ monomer and dimer were captured on Toyopearl SP-650 M equilibrated in 50 mM Mes-Na pH 6.5 (N-Morpholino ethanesulfonate) (Buffer A). The column was washed with 4 liters of buffer A, and eluted with 4 liters of linear gradient of 0–0.5 M NaCl in buffer A. Truncated groβ monomer was eluted during gradient and truncated groβ dimer was eluted with 1 M NaCl solution. Fractions containing truncated groβ monomer and dimer were pooled separately. Each pool was adjusted to pH 3.0 with 10% TFA solution, applied to Vydac C18 (2.1×25 cm) equilibrated with 0.1% TFA in 10% acetonitrile, and eluted with linear gradient of 10–40% acetonitrile in 0.1% TFA for 30 min. Truncated groβ monomer was eluted at ~27% acetonitrile. Truncated groβ dimer was eluted at ~31% to acetonitrile. Fractions containing truncated groβ was pooled, lyophilized to dryness to remove acetonitrile and TFA and solubilized in saline solution. Endotoxin level was 0.1 EU/mg.

Typical yield of truncated groβ monomer was ~2 mg/g of cells and groβ dimer was ~0.2 mg/g of cells.

D. Characterization

The molecular weight of the truncated groβ dimer as determined on nonreducing SDS-PAGE was approximately twice that of truncated groβ monomer.

Groβ dimer was boiled in 2% SDS with/without 100 mM DTT at pH 6.8 for 5 minutes. In SDS-PAGE, groβ dimer migrated as a dimer without DTT and as a monomer after treated with DTT. Upon reduction, both forms migrated to the same spot indicating that truncated groβ dimer is a disulfide linked dimer. Groβ dimer was mixed with saturated solution of sinapinic acid (3,5-dimethoxy-4 hydroxycinnamic acid) in 40% acetonitrile and 1% TFA and was analyzed in matrix-assisted laser desorption/ionization mass spectrometry, which gave the molecular mass of dimer. The molecular weight of truncated groβ dimer, as determined by MALD-MS analysis was 15,069 Da (predicted 15,073 Da), while that of truncated groβ monomer was 7,536 Da (predicted 7,537 Da). N-terminal sequencing of truncated groβ dimer showed that 2–3% of the final products retained the initiatory Met. Disulfide pairing pattern of truncated groβ dimer was the same as that of truncated groβ (C5–C31, C7–C47) [amino acids 5–73 of SEQ ID NO:3], however, all pairings were intermolecular rather than intramolecular. Gel filtration analysis and ultracentrifugation sedimentation equilibrium studies in PBS (pH 7.0) showed that truncated groβ dimer exhibited reversible assembly of octamer to hexadecamer at 0.25 mg/ml, while truncated groβ [amino acids 5–73 of SEQ ID NO:3] was a nonconvalent dimer even at 20 mg/ml. Concentration of truncated groβ monomer or dimer has been determined by quantitative amino acid analysis.

E. Purification of Truncated KC (Amino Acids 5–72 of SEQ ID NO:1)

DET-DDDDK KC was purified and refolded as described for truncated groβ. The refolded DET-DDDDK KC was digested with enterokinase to remove the N-terminal DET-DDDDK and the undigested molecules were removed using anti DET Mab column. The digested molecule was further purified using C18 RP-HPLC as described for groβ.

EXAMPLE 2

Prophylactically Administered Truncated KC in *E. Coli* Sepsis

The animals were dosed intraperitoneally with truncated KC [amino acids 5–72 of SEQ ID NO:1] at doses of 10, 33, 100 or 333 fg/kg 24 hours and 2 hours before infection. Control animals were dosed with dilution buffer on the same schedule. Starting two hours after infection the rats were treated twice daily with subcutaneous geltamicin. On day 0 the rats were implanted with an *E. coli* containing fibrin-thrombin clot. Starting two hours after infection the rats were treated with gentamicin twice daily. The rats prophylactically treated with truncated KC at 33 or 100 fg/kg followed by gentamicin treatment demonstrated significantly improved survival rates over the diluent treated control rat receiving gentamicin therapy alone.

Results

| Results | |
|---|---|
| Dose (fg/kg) | survival (alive/dead) |
| Control | 8/17 |
| 10 | 10/15 |
| 33 | 17/8 |
| 100 | 18/7 |
| 333 | 10/15 |

EXAMPLE 3

Therapeutically Administered Truncated KC in *E. Coli* Sepsis

On day 0 the rats were implanted with an *E. coli* containing fibrin-thrombin clot. The animals were dosed intraperitoneally with truncated KC [amino acids 5–72 of SEQ ID NO:1] at doses of 33, 100, 333, or 1,000 fg/kg as a single injection 2 hours after infection. Control animals were dosed with dilution buffer on the same schedule. Starting two hours after infection the rats were treated twice daily with subcutaneous gentamicin. The rats therapeutically treated with truncated KC at 100 or 333 fg/kg follow d by gentamicin treatment demonstrated significantly improved survival rates over the diluent treated control rat receiving gentamicin therapy alone.

Results

| Results | |
|---|---|
| Dose (fg/kg) | survival (alive/dead) |
| Control | 9/16 |
| 33 | 11/14 |
| 100 | 17/8 |
| 333 | 18/7 |
| 1,000 | 10/15 |

EXAMPLE 4

Therapeutically Administered Truncated KC in *S. Aureus* Sepsis

On day 0 the rats were implanted with a *S. aureus* containing fibrin-thrombin clot. The animals were dosed intraperitoneally with truncated KC [amino acids 5–72 of SEQ ID NO:1] at doses of 33, 100, 333, or 1,000 fg/kg as a single injection 2 hours after infection. Control animals were dosed with dilution buffer on the same schedule. Starting two hours after infection the rats were treated twice daily with subcutaneous gentamicin. The rats therapeutically treated with truncated KC at 100 or 333 fg/kg followed by gentamicin treatment demonstrated significantly improved survival rates over the diluent treated control rat receiving gentamicin therapy alone.

Results

| Results | |
|---|---|
| Dose (fg/kg) | survival (alive/dead) |
| Control | 8/17 |
| 33 | 11/14 |
| 100 | 17/8 |
| 333 | 21/4 |
| 1000 | 12/13 |

EXAMPLE 5

Therapeutically Administered Truncated Groβ in *S. Aureus* Sepsis

On day 0 the rats were implanted with an *S. aureus* containing fibrin-thrombin clot. The animals were dosed intraperitoneally with truncated groβ [amino acids 5–73 of SEQ ID NO:3] at doses of 33, 100, 333, or 1,000 fg/kg as a single injection 2 hours after infection. Control animals were dosed with dilution buffer on the same schedule. Starting two hours after infection the rats were treated twice daily with subcutaneous gentamicin. The rats therapeutically treated with truncated groβ at 100 or 333 fg/kg followed by gentamicin treatment demonstrated significantly improved survival rates over the diluent treated control rats receiving gentamicin therapy alone.

Results

| Results | |
|---|---|
| Dose (fg/kg) | survival |
| Control | 9/16 |
| 33 | 12/13 |
| 100 | 20/5 |

-continued

| Results | |
|---|---|
| Dose (fg/kg) | survival |
| 333 | 18/7 |
| 1,000 | 10/15 |

EXAMPLE 6

Therapeutical Subcutaneously Administered Truncated Groβ in *E. Coli* Sepsis

On day 0 the rats were implanted with an *E. coli* containing fibrin-thrombin clot. The animals were dosed subcutaneously with truncated groβ [amino acids 5–73 of SEQ ID NO:3] at doses of 0.1, 0.3, 1.0, or 3.3 pg/kg as a single injection 2 hours after infection. Control animals were dosed with dilution buffer on the same schedule. Starting two hours after infection the rats were treated twice daily with subcutaneous gentamicin. The rats therapeutically treated with truncated groβ at 0.3 or 1.0 pg/kg followed by gentamicin treatment demonstrated significantly improved survival rates over the diluent treated control rats receiving gentamicin therapy alone.

Results

| Results | |
|---|---|
| Dose (pg/kg) | survival (alive/dead) |
| Control | 10/15 |
| 0.1 | 12/13 |
| 0.3 | 18/7 |
| 1.0 | 20/5 |
| 3.3 | 11/14 |

EXAMPLE 7

Therapeutical Subcutaneously Administered Truncated Groβ in *S. Aureus* Sepsis

On day 0 the rats were implanted with an *S. aureus* containing fibrin-thrombin clot. The animals were dosed subcutaneously with truncated groβ [amino acids 5–73 of SEQ ID NO:3] at doses of 0.1, 0.3, 1.0, or 3.3 pg/kg as a single injection 2 hours after infection. Control animals were dosed with dilution buffer on the same schedule. Starting two hours after infection the rats were treated twice daily with subcutaneous septamicin. The rats therapeutically treated with truncated groβ at 0.3 or 1.0 pg/kg followed by gentamicin treatment demonstrated significantly improved survival rates over the diluent treated control rats receiving gentamicin therapy alone.

Results

| Results | |
|---|---|
| Dose (pg/kg) | survival (alive/dead) |
| Control | 8/17 |
| 0.1 | 13/12 |
| 0.3 | 18/7 |

-continued

| Results | |
|---|---|
| Dose (pg/kg) | survival (alive/dead) |
| 1.0 | 20/5 |
| 3.3 | 12/13 |

EXAMPLE 8

Prophylactically Administered GROβ Dimer in *E. Coli* Sepsis

The animals were dosed subcutaneously with dimer formed of two truncated groβ proteins [amino acids 5–73 of SEQ ID NO:3] at doses of 0.1, 0.3, 1.0 or 3.3 pg/kg 24 hours before infection. Control animals were doses with dilution buffer on the same schedule. On day 0 the rats were implanted with an *E. coli* containing fibrin-thrombin clot. Starting two hours after infection the rats were treated twice daily with subcutaneous gentamicin. The rats prophylactically treated with truncated groβ dimer at 0.3 or 1.0 pg/kg followed by gentamicin treatment demonstrated significantly improved survival rates over the diluent treated control rats receiving gentamicin therapy alone.

Results

| Results | |
|---|---|
| Dose (pg/kg) | survival (alive/dead) |
| Control | 8/17 |
| 0.1 | 10/15 |
| 0.3 | 18/7 |
| 1.0 | 20/5 |

EXAMPLE 9

Therapeutically Administered GROβ Dimer in *E. Coli* Sepsis

On day 0 the rats were implanted with an *E. Coli* containing fibrin-thrombin clot. The animals were dosed subcutaneously with a dimer formed of two truncated groβ proteins [amino acids 5–73 of SEQ ID NO:3] at doses of 0.03, 0.1, 0.3, 1.0, 3.3, or 10 pg/kg as a single injection 2 hours after infection. Control animals were doses with dilution buffer on the same schedule.

Starting two hours after infection the rats were treated twice daily with subcutaneous gentamicin. The rats therapeutically treated with truncated groβ dimer at 0.1, 0.3 or 1.0 pg/kg followed by gentamicin treatment demonstrated significantly improved survival rates over the diluent treated control rats receiving gentamicin therapy alone.

Results

| Results | |
|---|---|
| Dose (pg/kg) | survival (alive/dead) |
| Control | 11/14 |
| 0.03 | 12/13 |

-continued

| Results | |
|---|---|
| Dose (pg/kg) | survival (alive/dead) |
| 0.1 | 18/7 |
| 0.3 | 23/2 |
| 1.0 | 24/1 |
| 3.3 | 17/8 |
| 10.0 | 12/13 |

We claim:

1. A dimeric chemokine consisting of two covalently linked modified groβ proteins (consisting of amino acids 5–73 of SEQ ID NO: 3) wherein the proteins are linked by two intermolecular disulfide bonds between C9–C35 and C11–C51.

2. A pharmaceutical composition consisting of a chemokine of claim 1 and a pharmaceutically acceptable carrier.

* * * * *

SEQUENCE LISTING (1) GENERAL INFORMATION:

(iii) NUMBER OF SEQUENCES: 4

(2) INFORMATION FOR SEQ ID NO: 1:

(i) SEQUENCE CHARACTERISTICS:
      (A) LENGTH: 72 amino acids
      (B) TYPE: amino acid
      (C) STRANDEDNESS: <Unk nown>
      (D) TOPOLOGY: unknown (ii) MOLECULE TYPE: protein (xi) SEQUENCE DESCRIPTION: SEQ ID NO: 1:

```
Ala Pro Ile Ala Asn Glu Leu Arg Cys Gln C ys Leu Gln Thr Met
 1               5                  10                  15

Ala Gly Ile His Leu Lys Asn Ile Gln Ser L eu Lys Val Leu Pro
                20                  25                  30

Ser Gly Pro His Cys Thr Gln Thr Glu Val I le Ala Thr Leu Lys
                35                  40                  45

Asn Gly Arg Glu Ala Cys Leu Asp Pro Glu A la Pro Leu Val Gln
                50                  55                  60

Lys Ile Val Gln Lys Met Leu Lys Gly Val P ro Lys
                65                  70
```

(2) INFORMATION FOR SEQ ID NO: 2:

(i) SEQUENCE CHARACTERISTICS:
      (A) LENGTH: 73 amino acids
      (B) TYPE: amino acid
      (C) STRANDEDNESS: <Unk nown>
      (D) TOPOLOGY: unknown (ii) MOLECULE TYPE: protein (xi) SEQUENCE DESCRIPTION: SEQ ID NO: 2:

```
Ala Ser Val Ala Thr Glu Leu Arg Cys Gln C ys Leu Gln Thr Leu
 1               5                  10                  15

Gln Gly Ile His Pro Lys Asn Ile Gln Ser V al Asn Val Lys Ser
                20                  25                  30

Pro Gly Pro His Cys Ala Gln Thr Glu Val I le Ala Thr Leu Lys
                35                  40                  45

Asn Gly Arg Lys Ala Cys Leu Asn Pro Ala S er Pro Ile Val Lys
                50                  55                  60

Lys Ile Ile Glu Lys Met Leu Asn Ser Asp L ys Ser Asn
```

(2) INFORMATION FOR SEQ ID NO: 3:

(i) SEQUENCE CHARACTERISTICS:
        (A) LENGTH: 73 amino acids
        (B) TYPE: amino acid
        (C) STRANDEDNESS: <Unknown>
        (D) TOPOLOGY: unknown (ii) MOLECULE TYPE: protein (xi) SEQUENCE DESCRIPTION: SEQ ID NO: 3:

```
Ala Pro Leu Ala Thr Glu Leu Arg Cys Gln Cys Leu Gln Thr Leu
 1               5                  10                  15

Gln Gly Ile His Leu Lys Asn Ile Gln Ser Val Lys Val Lys Ser
                20                  25                  30

Pro Gly Pro His Cys Ala Gln Thr Glu Val Ile Ala Thr Leu Lys
                35                  40                  45

Asn Gly Gln Lys Ala Cys Leu Asn Pro Ala Ser Pro Met Val Lys
                50                  55                  60

Lys Ile Ile Glu Lys Met Leu Lys Asn Gly Lys Ser Asn
                65                  70
```

(2) INFORMATION FOR SEQ ID NO: 4:

(i) SEQUENCE CHARACTERISTICS:
        (A) LENGTH: 73 amino acids
        (B) TYPE: amino acid
        (C) STRANDEDNESS: <Unknown>
        (D) TOPOLOGY: unknown (ii) MOLECULE TYPE: protein (xi) SEQUENCE DESCRIPTION: SEQ ID NO: 4:

```
Ala Ser Val Val Thr Glu Leu Arg Cys Gln Cys Leu Gln Thr Leu
 1               5                  10                  15

Gln Gly Ile His Leu Lys Asn Ile Gln Ser Val Asn Val Arg Ser
                20                  25                  30

Pro Gly Pro His Cys Ala Gln Thr Glu Val Ile Ala Thr Leu Lys
                35                  40                  45

Asn Gly Lys Lys Ala Cys Leu Asn Pro Ala Ser Pro Met Val Gln
                50                  55                  60

Lys Ile Ile Glu Lys Ile Leu Asn Lys Gly Ser Thr Asn
                65                  70
```